United States Patent
Butler et al.

(10) Patent No.: US 7,569,741 B2
(45) Date of Patent: Aug. 4, 2009

(54) PETROCHEMICAL FEEDSTOCK PURIFICATION

(75) Inventors: James R. Butler, League City, TX (US); James T. Merrill, Katy, TX (US)

(73) Assignee: Fina Technology, Inc., Houston, TX (US)

(*) Notice: Subject to any disclaimer, the term of this patent is extended or adjusted under 35 U.S.C. 154(b) by 395 days.

(21) Appl. No.: 11/412,244

(22) Filed: Apr. 26, 2006

(65) Prior Publication Data
US 2006/0194993 A1 Aug. 31, 2006

Related U.S. Application Data

(63) Continuation-in-part of application No. 10/685,633, filed on Oct. 15, 2003, now abandoned.

(51) Int. Cl.
*C07C 7/10* (2006.01)
(52) U.S. Cl. ........................ 585/833; 585/449; 208/263; 208/254 R

(58) Field of Classification Search ............ None
See application file for complete search history.

(56) References Cited

U.S. PATENT DOCUMENTS

| | | | | |
|---|---|---|---|---|
| 4,009,217 A | * | 2/1977 | Uitti | 585/323 |
| 6,887,370 B2 | * | 5/2005 | De Wet et al. | 585/862 |
| 2003/0158456 A1 | * | 8/2003 | O'Rear et al. | 585/331 |
| 2003/0166982 A1 | * | 9/2003 | O' Rear et al. | 585/331 |

* cited by examiner

*Primary Examiner*—Tam M Nguyen
(74) *Attorney, Agent, or Firm*—Tenley R. Krueger

(57) ABSTRACT

Methods and systems for petrochemical feedstream purification are described herein. The methods generally include providing a petrochemical feedstock, wherein the petrochemical feedstock includes a concentration of polar impurities, contacting the petrochemical feedstock with a washing agent to remove at least a portion of the polar impurities therefrom, separating the washing agent from the petrochemical feedstock to form a purified feedstock and passing the purified feedstock to a petrochemical process. In one embodiment, the petrochemical feedstock includes benzene and the washing agent includes water.

14 Claims, 1 Drawing Sheet

PETROCHEMICAL FEEDSTOCK PURIFICATION

CROSS-REFERENCE TO RELATED APPLICATIONS

This application claims the benefit of U.S. Pat. application Ser. No. 10/685,633, filed Oct. 15, 2003.

FIELD

Embodiments of the present invention generally relate to purification of petrochemical feedstocks. In particular, embodiments of the invention relate to removal of impurities from alkylation feedstreams.

BACKGROUND

Petrochemical feedstocks, such as alkylation unit feedstocks, may include impurities. The impurities may have been added to one or more components of the respective stream in previous processing for a variety of purposes or the impurities may be present in raw materials, for example.

Unfortunately, petrochemical catalysts generally experience a reduction in activity upon exposure to reaction. The impurities may poison the catalyst, therefore requiring more frequent regeneration and/or replacement of such catalyst.

Therefore, a need exists to minimize the concentration of impurities in petrochemical feedstocks.

SUMMARY

Embodiments of the present invention include methods of feedstream purification. The methods generally include providing a petrochemical feedstock, wherein the petrochemical feedstock includes a concentration of polar impurities of at least 100 ppb, contacting the petrochemical feedstock with a washing agent to remove at least a portion of the polar impurities therefrom, separating the washing agent from the petrochemical feedstock to form a purified feedstock and passing the purified feedstock to a petrochemical process.

In another embodiment, the method includes providing an input stream including benzene, wherein the benzene has a concentration of polar impurities of at least 100 ppb, contacting the input stream with water for a period of time sufficient to remove at least a portion of the polar impurities therefrom, separating a water fraction from the benzene to form a purified alkylation feedstock, drying the purified alkylation feedstock, passing the purified alkylation feedstock to an alkylation system and contacting the purified alkylation feedstock with an alkylation catalyst to form an output stream including ethylbenzene.

One embodiment includes an alkylation system. The alkylation system generally includes a purification system including a first input, a first output, a second input and a second output, wherein the first input is adapted to receive benzene having polar impurities, the output is adapted to pass purified benzene therethrough and the second input and the second output are adapted to cycle a washing agent including water therethrough, a drying column in operable communication with the purification system and adapted to dry the purified benzene and an alkylation unit adapted to contact the purified benzene with an alkylation catalyst and ethylene to form ethylbenzene.

DETAILED DESCRIPTION

Introduction and Definitions

Figure 1:
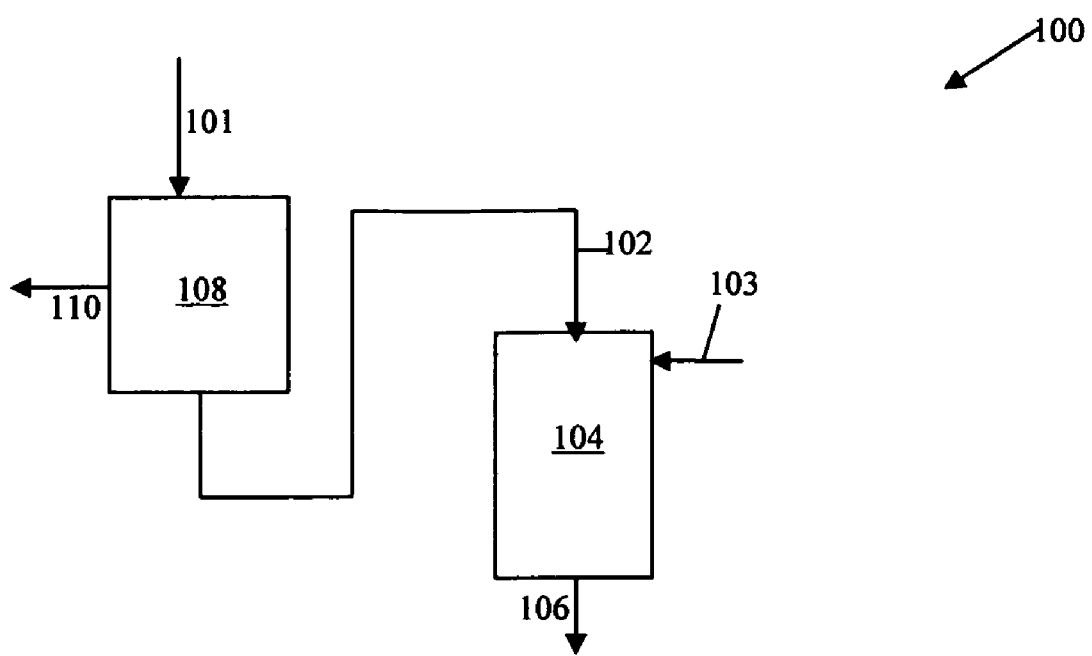
FIG. 1 illustrates an alkylation process.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

FIG. 1 illustrates a schematic block diagram of an embodiment of an alkylation process 100. Although not shown herein, the process stream flow may be modified based on unit optimization so long as the modification complies with the spirit of the invention, as defined by the claims. For example, at least a portion of any overhead fraction may be recycled as input to any other system within the process and/or any process stream may be split into multiple process stream inputs, for example. Also, additional process equipment, such as heat exchangers, may be employed throughout the processes described herein and such placement is generally known to one skilled in the art. Further, while described below in terms of primary components, the streams indicated below may include any additional components as known to one skilled in the art.

While embodiments of the invention are described in further detail below in terms of alkylation processes and feedstreams thereto, it is contemplated that the embodiments described herein may be utilized with any petrochemical feedstock having an unacceptable level of polar impurities, defined in further detail below.

The process 100 generally includes supplying a purified input 102 to an alkylation system 104. The alkylation system 104 is generally adapted to contact the purified input 102 with an alkylation catalyst to form an alkylation output stream 106. In addition to the purified input 102, an additional input, such as an alkylating agent, is generally supplied to the alkylation system 104 via line 103.

The purified input 102 generally includes a first aromatic compound. The aromatic compound may include substituted or unsubstituted aromatic compounds. If present, the substituents on the aromatic compounds may be independently selected from alkyl, aryl, alkaryl, alkoxy, aryloxy, cycloalkyl, halide and/or other groups that do not interfere with the alkylation reaction, for example. Examples of substituted aromatic compounds generally include toluene, xylene, isopropylbenzene, normal propylbenzene, alpha-methylnaphthalene, ethylbenzene, mesitylene, durene, cymene, butylbenzene, pseudocumene, o-diethylbenzene, m-diethylbenzene, p-diethylbenzene, isoamylbenzene, isohexylbenzene, pentaethylbenzene, pentamethylbenzene, 1,2,3,4-tetraethylbenzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, 4-ethyl-m-xylene, dimethylnaphthalenes, ethylnaphthalene, 2,3-dimethylanthracene, 9-ethylanthracene, 2-methylanthracene, o-methylanthracene, 9,10-dimethylphenanthrene and 3-methyl-phenanthrene. Further examples of aromatic compounds include hexylbenzene, nonylbenzene, dodecylbenzene, pentadecylbenzene, hexyltoluene, nonyltoluene, dodecyltoluene and pentadecytoluene. In one embodiment, the aromatic compound includes one or more hydrocarbons, such as benzene, naphthalene, anthracene, naphthacene, perylene, coronene and phenanthrene, for example. In another embodiment, the first aromatic compound includes benzene. The benzene may be supplied from a variety of sources, such as a fresh benzene source and/or a variety of recycle sources (e.g., alkylation recycle streams and/or streams from dehydrogenation processes,) for example.

As used herein, the term "fresh benzene source" refers to a source including at least about 95 wt. % benzene, at least about 98 wt. % benzene or at least about 99 wt. % benzene, for example.

The alkylating agent may include olefins (e.g., ethylene, propylene, butene and pentene), alcohols (e.g., methanol, ethanol, propanol, butanol and pentanol), aldehydes (e.g., formaldehyde, acetaldehyde, propionaldehyde, butyraldehyde and n-valeraldehyde) and/or alkyl halides (e.g., methyl chloride, ethyl chloride, propyl chloride, butyl chloride and pentyl chloride), for example. In one embodiment, the alkylating agent includes a mixture of light olefins, such as mixtures of ethylene, propylene, butene and/or pentenes, for example. In another embodiment, the alkylating agent includes ethylene.

The alkylation system 104 generally includes one or more reaction vessels. The reaction vessels may include continuous flow reactors (e.g., fixed-bed, slurry bed or fluidized bed,) for example. In one embodiment, the alkylation system 104 includes a plurality of multi-stage reaction vessels (not shown). For example, the plurality of multi-stage reaction vessels may include a plurality of operably connected catalyst beds, such beds containing an alkylation catalyst (not shown.) The number of catalyst beds is generally determined by individual process parameters, but may include from 2 to 20 catalyst beds or from 3 to 10 catalyst beds, for example.

Such reaction vessels may be liquid phase, vapor phase, supercritical phase or mixed phase reactors operated at reactor temperatures and pressures sufficient to maintain the alkylation reaction in the corresponding phase, i.e., the phase of the aromatic compound, for example. Such temperatures and pressures are generally determined by individual process parameters. In one embodiment, the plurality of stages within a reaction vessel may be operated with the same or different catalyst and at the same or different temperatures and space velocities. Such temperatures and pressures are generally determined by individual process parameters. However, liquid phase reactions may occur at temperatures of from about 160° C. to about 270° C. and pressures of from about 400 psig to about 700 psig, for example. Vapor phase reactions may occur at temperatures of from about 350° C. to about 500° C. and pressures of from about 200 psig to about 355 psig, for example.

The alkylation catalyst may include a molecular sieve catalyst. Such molecular sieve catalyst may include zeolite beta, zeolite Y, 25M-5, zeolite MCM-22, zeolite MCM-36, zeolite MCM-49 or zeolite MCM-56, for example. In one embodiment, the catalyst is a zeolite beta having a silica to alumina molar ratio (expressed as $SiO_2/Al_2O_3$) of from about 10 to about 200 or about 20 to about 50, for example. In one embodiment, the zeolite beta may have a low sodium content, e.g., less than about 0.2 wt. % expressed as $Na_2O$, or less than about 0.02 wt. %, for example. The sodium content may be reduced by any method known to one skilled in the art, such as through ion exchange, for example. (See, U.S. Pat. No. 3,308,069 and U.S. Pat. No. 4,642,226 (formation of zeolite beta), U.S. Pat. No. 4,185,040 (formation of zeolite Y), U.S. Pat. No. 4,992,606 (formation of MCM-22), U.S. Pat. No. 5,258,565 (formation of MCM-36), WO 94/29245 (formation of MCM-49) and U.S. Pat. No. 5,453,554 (formation of MCM-56.))

The alkylation catalyst may optionally be bound to, supported on or extruded with any support material. For example, the alkylation catalyst may be bound to a support to increase the catalyst strength and attrition resistance. The support material may include alumina, silica, aluminosilicate, titanium and/or clay, for example.

The alkylation output 106 generally includes a second aromatic compound formed from the reaction of the first aromatic compound and the alkylating agent in the presence of the alkylation catalyst, for example.

In a specific embodiment, the first aromatic compound includes benzene and the first alkylating agent includes ethylene, while the second aromatic compound includes ethylbenzene. In one embodiment, the molar ratio of benzene to ethylene entering the alkylation system 104 may be from about 1:1 to about 30:1, or from about 1:1 to about 20:1 or from about 2:1 to about 15:1 and the liquid hourly space velocity may be from about 2 to about 75, for example.

In addition to the first aromatic compound and the alkylating agent, the purified input 102. and/or line 103 may further include other compounds in minor amounts, such as $C_7$ aliphatic compounds and/or nonaromatic compounds, for example. In one embodiment, the purified input 102 includes less than about 3% of such compounds or less than about 1%, for example.

In addition, the purified input 102 and/or line 103 may include polar impurities, such as nitrogen containing compounds (e.g., amines), thiols, alcohols, ketones and organo sulfur compounds. The polar impurities may be present in commercially supplied feedstocks or may have been added to one or more components of the respective stream in previous processing, such as dehydrogenation, for a variety of purposes, for example. For example, the polar impurities may have been added to the components (e.g., the first aromatic compound) as polymerization inhibitors and/or neutralizers, for example.

Unfortunately, alkylation and transalkylation catalysts generally experience deactivation upon exposure to reaction. The polar impurities may further poison the alkylation catalyst, therefore requiring more frequent regeneration and/or replacement of such catalyst.

Therefore, embodiments of the invention generally include subjecting at least a portion of the purified input 102 to purification via line 101. While FIG. 1 illustrates purifying the purified input 102, it is contemplated that any stream entering the alkylation unit 104 may be exposed to a washing process 108, such as line 103 and/or any recycle streams.

Line 101 generally includes any first aromatic compound containing polar impurities. For example, line 101 may include the first aromatic compound from purified input 102, recycle first aromatic compound or combinations thereof. In one embodiment, line 101 includes benzene.

The purification process 108 generally includes contacting line 101 with a washing agent. In one embodiment, the washing agent includes water. The water may be supplied from any source suitable for entrainment of polar impurities. For example, the water may include deionized water, boiler feed water, steam condensate, steam stripped wash water or combinations thereof, for example. In one embodiment, the water has a minimal amount of water treatment residuals.

The washing agent may contact the feedstock 101 in an amount of from about 1 wt. % to about 100 wt. % or from about 2 wt. % to about 40 wt. %, for example. The amount of washing agent may include any amount to provide a specified reduction in polar impurities. For example, the water may be supplied in an amount of from about 10,000 ppm to about 100,000 ppm.

The contact may occur in any manner known to one skilled in the art. For example, the contact may occur in a single stage (e.g., a tank) or in an extraction unit (e.g., multiple stages.)

The washing agent may contact the feedstock 101 for a time sufficient to provide a specified reduction in polar impurities. For example, the residence time may be from about 0.01 seconds to about 1 minute, or less than about 5 minutes, or less than about 10 hours, for example. In one embodiment, the washing agent and the feedstock 101 may have increased contact. For example, the washing agent and the feedstock 101 may be mixed and/or agitated, for example, to increase the contact therebetween.

The residence time (e.g., contact time) may vary depending on the number of stages. For example, the residence time per stage may be from about 0.01 second to about 5 minutes, for example. The number of stages may be from about 1 to about 100, for example. In addition, the contact temperature may be from about room temperature to about 200° C., such as ambient temperature, for example.

Upon purification, the washing agent is removed from the feedstock 101 via methods known to one skilled in the art, such as extraction. The washing agent fraction may be used for any suitable purpose or subjected to wastewater treatment, for example. Prior to use or treatment the washing agent fraction may further be subjected to steam stripping or extraction, for example.

The purified input may further be dried and passed to the alkylation unit via line 102, for example. The specified reduction in polar impurities will vary depending upon the application and amount of polar impurities. However, in one embodiment, the polar impurities removal is greater than about 90%. Embodiments of the invention result in an unexpected significant decrease in the amount of polar impurities. For example, in one embodiment, the purified input 102 includes less than about 50 ppb nitrogen or less than about 30 ppb nitrogen, for example.

As is known to one skilled in the art and previously discussed, the purified input 102 may undergo further treatment prior to entering the alkylation unit 104, such as drying, for example.

One specific embodiment includes an alkylation system. The alkylation system generally includes a purification system including a first input, a first output, a second input and a second output, wherein the first input is adapted to receive benzene having polar impurities, the output is adapted to pass purified benzene therethrough and the second input and the second output are adapted to cycle a washing agent including water therethrough, a drying column in operable communication with the purification system and adapted to dry the purified benzene and an alkylation unit adapted to contact the purified benzene with an alkylation catalyst and ethylene to form ethylbenzene.

The life of the catalyst generally depends on process conditions and catalyst type. However, when regeneration of any catalyst within the system is desired, the regeneration procedure generally includes processing the deactivated catalyst at high temperatures, although the regeneration may include any regeneration procedure known to one skilled in the art.

Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the catalyst to a temperature or a series of temperatures, such as a regeneration temperature of from about 50° C. to about 400° C. above the purging or reaction temperature, for example.

In one specific non-limiting embodiment, the alkylation catalyst is heated to a first temperature (e.g., 700° F.) with a gas containing nitrogen and about 2% oxygen, for example, for a time sufficient to provide an output stream having an oxygen content of about 0.5%. The catalyst may then be heated to a second temperature for a time sufficient to provide an output stream having an oxygen content of about 2.0%. The second temperature may be about 50° F. greater than the first temperature, for example. The second temperature is generally about 950° F. or less, for example. The catalyst may further be held at the second temperature for a period of time, or at a third temperature that is greater than the second temperature, for example.

Upon catalyst regeneration, the catalyst may then be reused for alkylation and transalkylation, for example.

While the foregoing is directed to embodiments of the present invention, other and further embodiments of the invention may be devised without departing from the basic scope thereof and the scope thereof is determined by the claims that follow.

What is claimed is:

1. A method of feedstream purification comprising:
providing a petrochemical feedstock, wherein the petrochemical feedstock comprises polar impurities, wherein the polar impurities are selected from amines, thiols, alcohols, ketones, organo sulfur compounds and combinations thereof and wherein the petrochemical feedstock comprises an alkylation feedstock comprising benzene;
contacting the petrochemical feedstock with a washing agent to remove at least a portion of the polar impurities therefrom;
separating the washing agent from the petrochemical feedstock to form a purified feedstock; and
passing the purified feedstock to an alkylation process.

2. The method of claim 1, wherein the washing agent comprises water.

3. The method of claim 1, wherein from about 10,000 ppm to about 100,000 ppm of washing agent contact the petrochemical feedstock.

4. The method of claim 1, wherein the purified feedstock comprises less than about 30 ppb of polar impurities.

5. The method of claim 1, wherein the purified feedstock comprises an undetectable nitrogen concentration.

6. The method of claim 1, wherein the petrochemical feedstock is contacted with the washing agent at a concentration of washing agent to petrochemical feedstock of from about 0.1 wt.% to about 100 wt.%.

7. The method of claim 1, wherein the petrochemical feedstock is contacted with the washing agent at a concentration of washing agent to petrochemical feedstock of from about 2 wt.% to about 40 wt.%.

8. The method of claim 1, wherein the petrochemical feedstock is contacted with the washing agent for a time of from about 0.01 seconds to about 10 hours.

9. The method of claim 1, wherein the petrochemical feedstock is contacted with the washing agent for a time of from about 0.01 seconds to about 5 minutes.

10. The method of claim 1, wherein the petrochemical feedstock is contacted with the washing agent in a plurality of stages.

11. The method of claim 10, wherein the petrochemical feedstock contacts the washing agent for a time of from about 0.01 seconds to about 5 minutes per stage.

12. The method of claim 1, wherein the petrochemical feedstock is contacted with the washing agent in an extraction unit.

13. The method of claim 1, wherein the petrochemical feedstock is contacted with the washing agent in a tank.

14. The method of claim 1 further comprising drying the purified feedstock prior to passing to the petrochemical process.

* * * * *